United States Patent [19]

Imi et al.

[11] Patent Number: 5,637,751

[45] Date of Patent: Jun. 10, 1997

[54] PROCESS FOR PRODUCING 1,4-DICYANO-2-BUTENE AND CATALYST THEREFOR

[75] Inventors: Katsuharu Imi, Shiga-ken; Shigeo Wake, Saijo, both of Japan

[73] Assignee: Sumitomo Chemical Company, Limited, Osaka, Japan

[21] Appl. No.: 40,439

[22] Filed: Apr. 1, 1993

[30] Foreign Application Priority Data

Apr. 1, 1992 [JP] Japan ................................ 4-079615
Aug. 10, 1992 [JP] Japan ................................ 4-212502

[51] Int. Cl.$^6$ .................................................. C07C 253/16
[52] U.S. Cl. ................................................ 558/350; 558/339
[58] Field of Search ................................... 558/350, 339

[56] References Cited

U.S. PATENT DOCUMENTS 3,711,527  1/1973  Kurtz ........................ 260/465.8
4,317,781  3/1982  Hutton ........................... 558/350

FOREIGN PATENT DOCUMENTS 857374   7/1949  Germany .
1906493  8/1970  Germany .
2144390  9/1971  Germany .
2723778  5/1977  Germany .
1384796  2/1975  United Kingdom .

*Primary Examiner*—Johann Richter
*Assistant Examiner*—John Peabody
*Attorney, Agent, or Firm*—Birch, Stewart, Kolasch & Birch, LLP

[57] ABSTRACT

2-Butene-1,4-diol and/or 3-butene-1,2-diol are (is) reacted with hydrogen cyanide in the presence of a molten catalyst comprising a cuprous halide and a non-aromatic organic amine hydrohalide.

18 Claims, No Drawings

PROCESS FOR PRODUCING 1,4-DICYANO-2-BUTENE AND CATALYST THEREFOR

The present invention relates to a process for producing 1,4-dicyano-2-butene. 1,4-Dicyano-2-butene is a material for synthesizing hexamethylenediamine, which is a material for 6,6-nylon and other products.

German Patent No. 2,128,001 discloses a process for producing 1,4-dicyano-2-butene which comprises reacting 2-butene-1,4-diol with hydrogen cyanide in a gas phase by using a catalyst comprising a cuprous halide supported on silica gel or the like. German Patent No. 2,144,390 discloses a process for producing 1,4-dicyano-2-butene by reacting 2-butene-1,4-diol with hydrogen cyanide in a liquid phase in the presence of a catalyst comprising copper bromide and an alkali metal bromide.

Japanese Patent Kokoku (Post-Exam. Publn.) No. 47-29,888 discloses a process for producing 1,4-dicyano-2-butene by reacting 1,4-diacetoxy-2-butene with hydrogen cyanide in the presence of a catalyst comprising a cuprous halide and a non-aromatic organic amine hydrohalide. Another known process comprises cyanation of 1,4-diacetoxy-2-butene with the aid of a catalyst based on a cuprous halide (Japanese Patent Kokoku (Post-Exam. Publn.) No. 47-29,888 and German Patent No. 2,723,778).

In the reactions of 2-butene-1,4-diol with hydrogen cyanide of the prior art processes, however, the gas phase reactions form a large amount of oligomers and other impurities and hence give a low yield; while, among the liquid phase reaction, those of aqueous solution system give a poor volume efficiency and hence are unfavorable from the industrial viewpoint. In the reaction of 1,4-diacetoxy-2-butene with hydrogen cyanide, on the other hand, the reaction velocity is not sufficiently high and the reaction difficultly goes to completion. In the reaction, further, acetic acid must be recovered from the reaction system, which raises operational difficulty in industrial practice.

In view of such circumstances, the present inventors have made extensive study to find an industrially advantageous process for producing 1,4-dicyano-2-butene, and resultantly found that when 2-butene-1,4-diol or 3-butene-1,2-diol, or both, were reacted with hydrogen cyanide in the presence of a catalyst comprising a cuprous halide and a non-aromatic organic amine hydrohalide, the reaction proceeds very rapidly to produce 1,4-dicyano-2-butene with good selectivity. The inventors have further found that the catalyst can be recycled and reused by removing water from the catalyst and further that the deterioration of catalyst can be suppressed by removing water from the catalyst and reacting a hydrohalogenic acid on the used catalyst (namely, the catalyst used once or more).

Thus, the present invention relates to a process for producing 1,4-dicyano-2-butene which comprises the step of reacting 2-butene-1,4-diol and/or 3-butene-1,2-diol with hydrogen cyanide in the presence of a catalyst comprising a cuprous halide and a non-aromatic organic amine hydrohalide. Further, the invention relates to a process for producing 1,4-dicyano-2-butene which comprises the step of reacting 2-butene-1,4-diol and/or 3-butene-1,2-diol with hydrogen cyanide in the presence of a catalyst comprising a cuprous halide and a non-aromatic organic amine hydrohalide and the step of removing water from used catalyst and then reusing the resulting catalyst. The invention also relates to a process further comprising the step of removing water from the used catalyst and reacting a hydrohalogenic acid on the used catalyst.

The 2-butene-1,4-diol or the 3-butene-1,2-diol used in the present invention can be easily obtained by the hydrolysis of a diacetoxybutene, which may be prepared from butadiene and acetic acid by a known method. In the reaction of the present invention, they may be used either as such alone or as a mixture.

In the process of the present invention, hydrocyanic acid of a high concentration (having a water content of 10% by weight or less) is preferably used. It is of course possible to use anhydrous hydrogen cyanide.

The catalyst comprises a cuprous halide and a non-aromatic organic amine hydrohalide.

The cuprous halide is preferably the chloride or the bromide. These may be used each alone or as a mixture thereof.

The non-aromatic organic amine hydrohalide are preferably those which can form an anhydrous molten mixture with a cuprous halide. Examples of such salts include ammonium halides such as ammonium chloride and ammonium bromide; the hydrochlorides or hydrobromides of lower alkylamines, such as methylamine, dimethylamine, trimethylamine, ethylamine, diethylamine and triethylamine; and the hydrochlorides or hydrobromides of amines having a functional group inert to the reaction, such as ethanolamine, diethanolamine and ethylenediamine. Preferred among them are the hydrochlorides or hydrobromides of lower alkyl(C1–C6) amines. These non-aromatic organic amine hydrohalide may be used each alone or as a mixture thereof.

The cuprous halide and the non-aromatic organic amine hydrohalide are used in a molar ratio of 1:3~3:1, preferably 1:1.5~1.5:1.

The catalyst is preferably used in rather large amount in consideration of the reaction velocity. In ordinary reactions, the amount may be about 10–200% by mole. The reaction temperature may be in the range of about 20°–200° C., preferably about 60°–140° C. The present reaction is preferably conducted in a liquid phase, suspension state or emulsion state, optionally under applied pressure. The reaction is desirably conducted in an atmosphere of inert gas, such as nitrogen, from the viewpoint of suppressing the oxidation of the copper component in the catalyst.

The reaction product is subjected to after-treatments in a conventional manner. Usually the intended product is extracted with a solvent, such as ethyl acetate and toluene, and then the solvent is distilled off. If necessary and desired, the product may be subjected to further purification treatments, such as distillation or recrystallization.

The used catalyst can be reused as the catalyst after removing the water formed by the reaction and contained therein by such means as vacuum distillation. The used catalyst will solidify when allowed to stand at room temperature for a long time. Usually the regenerating operation of the catalyst are conducted at a temperature higher than room temperature, preferably at 30°–70° C. The regeneration and reuse of the catalyst can be conducted repeatedly.

As the catalyst is reused repeatedly, insoluble substances comprising copper cyanide as the main component come to separate out from the reaction mixture. Further, both the conversion of raw materials and the selectivity to the intended product become lower.

The deterioration of the catalyst mentioned above can be suppressed by the addition of a hydrohalogenic acid. The hydrohalogenic acid may be hydrochloric acid, hydrobromic acid, and the like. They can be used in any of the forms of aqueous solution, gas, and solution in an organic solvent. The amount of the hydrohalogenic acid used is preferably about 0.01–0.1 mole relative to 1 mole of the cuprous halide.

The hydrohalogenic acid may be added either to the reaction mixture after completion of the reaction or to the used catalyst, including the insoluble substances, after separation of the intended product. Further, it may be added to the insoluble substance formed through the deterioration of the catalyst. The addition of the hydrohalogenic acid to the used catalyst may be conducted either before the removal of water or after the removal.

In the present reaction., a monocyano-compound (1-cyano-2-butene-4-ol) is also formed in the course of reaction and is further converted to a dicyano compound (1,4-dicyano-2-butene). Accordingly, it is also possible to use the monocyano compound as the starting material, and this embodiment is included in the present invention.

According to the process of the present invention, 1,4-dicyano-2-butene can be obtained in a good yield, high reaction velocity and good volume efficiency. Further, the reaction product can be easily after-treated and the production facilities can be simplified. Moreover, the catalyst can be recycled and reused, so that the consumption of the catalyst can be reduced.

The present invention will be described in more detail below with reference to Examples, but the invention is in no way limited thereto. In the Examples, the "purity" refers to the content of 1,4-dicyano-2-butene in the crude product and the "yield" to the value calculated in terms of the pure product.

EXAMPLE 1

Cuprous chloride (15 g, 0.15 mole) and trimethylamine hydrochloride (15 g, 0.16 mole) were heated at 80° C. with stirring to prepare a molten catalyst. Then a mixture of 2-butene-1,4-diol (22 g, 0.25 mole) and hydrogen cyanide (20 ml, 0.5 mole) was added dropwise into the catalyst at 80° C. over a period of 3 hours. The resulting reaction mixture was kept at 80° C. for further 3 hours and then extracted three times with 50 ml of ethyl acetate at 30°–40° C. Then the solvent was evaporated off under reduced pressure to obtain 26 g (yield: 86%, purity: 88%) of a crude 1,4-dicyano-2-butene.

EXAMPLE 2

Cuprous chloride (5 g, 0.05 mole) and trimethylamine hydrochloride (4.8 g, 0.05 mole) were heated at 80° C. with stirring to prepare a molten catalyst. Then a mixture of 3-butene-1,2-diol (8.8 g, 0.1 mole) and hydrogen cyanide (7.6 ml, 0.2 mole) was added dropwise into the catalyst at 80° C. over a period of 4 hours. The resulting reaction mixture was kept at 80° C. for further 2 hours and then extracted three times with 30 ml of ethyl acetate at 30°–40° C. Then the solvent was evaporated off under reduced pressure to obtain 10.2 g (yield: 78%, purity: 81%) of a crude 1,4-dicyano-2-butene. The analysis of the product by gas chromatography revealed that scarcely no other isomer was present.

EXAMPLE 3

Cuprous chloride (9.9 g, 0.1 mole) and triethylamine hydrochloride (13.8 g, 0.1 mole) were heated at 80° C. with stirring to prepare a molten catalyst. Then a mixture of 2-butene-1,4-diol (17.6 g, 0.2 mole) and hydrogen cyanide (15.2 ml, 0.2 mole) was added dropwise into the catalyst at 80° C. over a period of 4 hours. The resulting reaction mixture was kept at 80° C. for further 2 hours and extracted twice with 30 ml of ethyl acetate at 30°–40° C. Then the solvent was evaporated off under reduced pressure to obtain 26 g (yield: 70%, purity 57%) of a crude 1,4-dicyano-2-butene.

EXAMPLE 4

The same procedures as in Example 3 were followed except for using cuprous bromide (14.3 g, 0.1 mole) and trimethylamine hydrochloride (9.6 g, 0.1 mole) in place of cuprous chloride (9.9 g, 0.1 mole) and triethylamine hydrochloride (13.8 g, 0.1 mole), to obtain 20.3 g (yield: 68%, purity: 71%) of a crude 1,4-dicyano-2-butene.

EXAMPLE 5

Cuprous chloride (99 g, 1.0 mole), trimethylamine hydrochloride (96 g, 1.0 mole) and copper powder (0.2 g) were heated at 80° C. with stirring to prepare a molten catalyst. Then a mixture of 2-butene-1,4-diol (88 g, 1.0 mole) and hydrogen cyanide (76 ml, 2.0 moles) was added dropwise into the catalyst at 80° C. over a period of 4 hours. The resulting reaction mixture was kept at 80° C. for further 2 hours and then extracted 5 times with 100 ml of toluene at 70°–80° C. Then the solvent was evaporated off under reduced pressure to obtain a crude 1,4-dicyano-2-butene. After the extraction, the used catalyst was recovered, water was removed therefrom under reduced pressure at 70°–80° C. and the resulting catalyst liquid was recycled for use in the next reaction. The results of the reactions are shown in Table 1.

It can be seen that extraction with ethyl acetate give high yields as compared with extraction with toluene.

TABLE 1

| Number of times of recycle | 1 | 2 | 3 | 4 | 5 | 6 |
|---|---|---|---|---|---|---|
| Yield (%) | 37 | 53 | 66 | 69 | 60 | 58 |
| Purity (%) | 77 | 87 | 82 | 81 | 72 | 66 |

EXAMPLE 6

The same procedures as in Example 5 were followed except that, in place of recovering the used catalyst and removing water therefrom under reduced pressure at 70°–80° C., the used catalyst was recovered, 2 g (0.02 mole) of concentrated hydrochloric acid was added thereto at 70°–80° C., the resulting mixture was kept at the temperature for 30 minutes and then water was removed therefrom. The results thus obtained are shown in Table 2.

TABLE 2

| Number of times of recycle | 1 | 2 | 3 | 4 | 5 | 6 |
|---|---|---|---|---|---|---|
| Yield (%) | 34 | 56 | 64 | 69 | 69 | 74 |
| Purity (%) | 88 | 88 | 84 | 87 | 86 | 84 |

COMPARATIVE EXAMPLE 1

Cuprous chloride (15 g, 0.15 mole) and trimethylamine hydrochloride (15 g, 0.16 mole) were heated at 80° C. with stirring to prepare a molten catalyst. Then a mixture of 1,4-diacetoxy-2-butene (43 g, 0.25 mole) and hydrogen cyanide (20 ml, 0.5 mole) was added dropwise into the catalyst liquid at 80° C. over a period of 3 hours and the resulting mixture was kept at 80° C. for further 1 hour. Since the progress of the reaction was found to be slow upon gas-chromatographic analysis, the mixture was heated to 100° C. and 10 ml of hydrogen cyanide was further added thereto. The resulting reaction mixture was kept at 100° C.

for further 4 hours and then extracted three times with 50 ml of ethyl acetate at 30°–40° C. Then the solvent was evaporated off under reduced pressure to obtain 28 g (yield: 83%, purity: 78%) of a crude 1,4-dicyano-2-butene. Analysis by gas chromatography revealed that the product contained remaining starting materials and mono-cyanogenated compounds.

What is claimed is:

1. A process for producing 1,4-dicyano-2-butene which comprises the step of reacting in liquid phase 2-butene-1,4-diol and/or 3-butene-1,2-diol with hydrogen cyanide in the presence of a molten catalyst comprising (1) cuprous chloride or cuprous bromide and (2) a non-aromatic amine hydrohalide selected from the group consisting of ammonium chloride, ammonium bromide, a hydrochloride of a lower alkylamine, a hydrobromide of a lower alkylamine, a hydrochloride of an amine having a functional group inert to the reaction, a hydrobromide of an amine having a functional group inert to the reaction, and mixtures thereof, wherein the cuprous chloride or bromide and the non-aromatic amine hydrohalide are present in a molar ratio of 1:3 to about 3:1, and wherein water is produced as a byproduct.

2. The process according to claim 1 which further comprises the step of removing from the used catalyst the water contained therein and reusing the resulting catalyst.

3. The process according to claim 1 which further comprises the step of removing from the used catalyst the water contained therein, then reacting the catalyst with a hydrohalogenic acid and reusing the resulting catalyst.

4. The process according to claim 1 which further comprises the step of reacting the used catalyst with a hydrohalogenic acid, then removing from the catalyst the water contained therein and reusing the resulting catalyst.

5. The process according to claim 1 wherein the lower alkylamine is a lower alkylamine of 1–6 carbon atoms.

6. A process for producing 1,4-dicyano-2-butene which comprises the step of reacting 2-butene-1,4-diol and/or 3-butene-1,2-diol with hydrogen cyanide in a liquid phase in the presence of a molten mixture catalyst comprising a cuprous halide and a non-aromatic amine hydrohalide.

7. The process according to claim 1, wherein said hydrogen cyanide is present in the form of hydrocyanic acid having a water content of 10% by weight or less.

8. The process according to claim 1, wherein the non-aromatic amine hydrohalide is selected from the group consisting of ammonium chloride, ammonium bromide, methylamine, dimethylamine, trimethylamine, ethylamine, diethylamine, triethylamine, ethanolamine, diethanolamine, and ethylendiamine.

9. The process according to claim 1, wherein the non-aromatic amine hydrohalide is selected from the group consisting of hydrochlorides and hydrobromides of lower alkyl amines.

10. The process according to claim 1, wherein the cuprous chloride or bromide and the non-aromatic amine hydrohalide are present in a molar ratio of 1:1.5 to about 1.5:1.

11. The process according to claim 1, wherein the reaction temperature is in the range of 20° to 200° C.

12. The process according to claim 1, wherein the reaction temperature is in the range of 60° to 140° C.

13. The process according to claim 3, wherein the hydrohalogenic acid is hydrochloric acid or hydrobromic acid.

14. The process according to claim 3, wherein the amount of hydrohalogenic acid is 0.01–0.1 moles relative to one mole of the cuprous chloride or bromide.

15. The process according to claim 1, wherein said hydrogen cyanide is anhydrous.

16. The process according to claim 1, wherein the catalyst is present in an amount of 10–200% by mole of 1,4-dicyano-2-butene.

17. The process according to claim 1, wherein the process is conducted without the addition of water.

18. The process according to claim 1, which further comprises removing water from the catalyst after removal of the 1,4-dicyano-2-butene product.

* * * * *